US 9,877,526 B2

(12) United States Patent
Haas et al.

(10) Patent No.: US 9,877,526 B2
(45) Date of Patent: *Jan. 30, 2018

(54) CONTROLLABLE THERMAL WARMING DEVICES

(76) Inventors: William S. Haas, Bartonville, IL (US); William J. Haas, Flower Mound, TX (US)

(*) Notice: Subject to any disclaimer, the term of this patent is extended or adjusted under 35 U.S.C. 154(b) by 1595 days.

This patent is subject to a terminal disclaimer.

(21) Appl. No.: 13/338,180

(22) Filed: Dec. 27, 2011

(65) Prior Publication Data

US 2012/0228279 A1 Sep. 13, 2012

Related U.S. Application Data

(63) Continuation-in-part of application No. 11/162,615, filed on Sep. 16, 2005, now Pat. No. 8,084,722, which
(Continued)

(51) Int. Cl.
*H05B 3/16* (2006.01)
*H05B 3/34* (2006.01)
(Continued)

(52) U.S. Cl.
CPC .......... *A41D 13/0051* (2013.01); *A61F 7/007* (2013.01); *B41J 2/375* (2013.01);
(Continued)

(58) Field of Classification Search
CPC ......... A41D 13/0051; A61F 2007/0001; A61F 2007/0233; B41J 2/375; H05B 1/02;
(Continued)

(56) References Cited

U.S. PATENT DOCUMENTS 3,422,244 A * 1/1969 Lauck ............................ 219/212
5,148,002 A * 9/1992 Kuo et al. ..................... 219/211
(Continued)

OTHER PUBLICATIONS

First 2 Pages of Exclusive License Agreement (ELA) (A) between Applicant and a Limited Liabilty Company listing Patents owned by Applicant—Dated—Mar. 2012.
(Continued)

*Primary Examiner* — Sang Y Paik

(57) ABSTRACT

A controllable thermal warming device for delivering heat to an object by radio frequency signal. The controllable thermal warming device may include a thermal ink heating element comprising a substrate and a conductive ink fixedly disposed on the substrate, a power source operatively coupled to the conductive ink, the power source adapted to deliver a voltage to the conductive ink to cause the conductive ink to radiate heat, a controller operatively coupled to the power source and the conductive ink, the controller adapted to control the voltage delivered to the conductive ink and to detect an operating characteristic of the conductive ink and adjust the voltage in response to the operating characteristic, and means for controlling the controller by radio frequency. The controllable thermal warming device may also include a sensor to provide the operating characteristic to the controller.

30 Claims, 11 Drawing Sheets

Related U.S. Application Data is a continuation-in-part of application No. 10/910,443, filed on Aug. 3, 2004, now abandoned, which is a continuation-in-part of application No. 10/854,838, filed on May 27, 2004, now Pat. No. 7,022,950, and a continuation-in-part of application No. 10/115,846, filed on Apr. 3, 2002, now Pat. No. 6,770,848.

(60) Provisional application No. 60/473,349, filed on May 27, 2003, provisional application No. 60/284,837, filed on Apr. 19, 2001, provisional application No. 60/494,023, filed on Aug. 11, 2003, provisional application No. 60/578,100, filed on Jun. 8, 2004.

(51) Int. Cl.

| | |
|---|---|
| *A41D 13/005* | (2006.01) |
| *A61F 7/00* | (2006.01) |
| *B41J 2/375* | (2006.01) |
| *H05B 1/02* | (2006.01) |
| *H05B 3/84* | (2006.01) |
| *A61F 7/02* | (2006.01) |

(52) U.S. Cl.
CPC ............ *H05B 1/02* (2013.01); *H05B 1/0208* (2013.01); *H05B 1/0272* (2013.01); *H05B 3/342* (2013.01); *H05B 3/84* (2013.01); *H05B 3/845* (2013.01); *A61F 2007/0001* (2013.01); *A61F 2007/0071* (2013.01); *A61F 2007/0233* (2013.01); *H05B 2203/013* (2013.01); *H05B 2203/017* (2013.01); *H05B 2203/022* (2013.01); *H05B 2203/026* (2013.01); *H05B 2203/029* (2013.01); *H05B 2203/036* (2013.01)

(58) Field of Classification Search
CPC ............ H05B 1/0272; H05B 2203/013; H05B 2203/017; H05B 2203/029; H05B 2203/036; H05B 3/342; H05B 3/84
USPC ................ 219/202, 203, 211, 212, 504, 505, 219/527–529, 542–549
See application file for complete search history.

(56) References Cited

U.S. PATENT DOCUMENTS

| | | | | |
|---|---|---|---|---|
| 5,321,229 | A | * | 6/1994 | Holling et al. ............ 219/445.1 |
| 5,496,989 | A | * | 3/1996 | Bradford et al. ............. 219/497 |
| 5,624,591 | A | * | 4/1997 | Di Trapani ................... 219/522 |
| 5,961,869 | A | * | 10/1999 | Irgens ........................... 219/549 |
| 6,024,904 | A | * | 2/2000 | Nanri ............................ 264/104 |
| 6,078,025 | A | * | 6/2000 | Yeung .......................... 219/211 |
| 6,172,335 | B1 | * | 1/2001 | Goodrich ...................... 219/251 |
| 6,389,681 | B1 | * | 5/2002 | Rock et al. ..................... 29/611 |

OTHER PUBLICATIONS

First page of Exclusive License Agreement (ELA) (B) between Applicant and a Limited Liability Company listing Patents owned by Applicant—Dated—Oct. 2012.

* cited by examiner

CONTROLLABLE THERMAL WARMING DEVICES

CROSS-REFERENCE TO RELATED APPLICATIONS

This application is a continuation-in-part of application Ser. No. 11/162,615 filed Sep. 16, 2005, which is a continuation-in-part of application Ser. No. 10/910,443 filed Aug. 3, 2004, which has issued to U.S. Pat. No. 7,022,950 on Apr. 4, 2006, which is a continuation-in-part of Ser. No. 10/854,838 filed May 27, 2004, which claims benefit to U.S. provisional application 60/473,349 filed on May 27, 2003 and is a continuation-in-part of Ser. No. 10/115,846 filed Apr. 3, 2002, which has issued to U.S. Pat. No. 6,770,848 on Aug. 3, 2004 and claims benefit to provisional application Ser. No. 60/284,837 filed Apr. 19, 2001. Application Ser. No. 10/910,443 also claims benefit to provisional patent application Ser. No. 60/494,023 filed on Aug. 11, 2003 and provisional patent application Ser. No. 60/578,100 filed on Jun. 8, 2004. The disclosures set forth in the referenced applications are incorporated herein by reference in their entirety.

FIELD

This disclosure relates generally to controllable thermal warming devices, and more particularly to controllable thermal warming devices controllable by radio frequency signal.

BACKGROUND

Heating elements of various constructions and configurations are heretofore known. Additionally, heating elements have been used in many different applications. An example of a heating element construction is disclosed in U.S. Pat. No. 6,189,487 to Owen.

SUMMARY

The present disclosure comprises one or more of the following features or combinations thereof disclosed herein or in the Detailed Description below.

The present disclosure relates to a controllable thermal warming device and means for controlling the thermal warming device by radio frequency signal. The controllable thermal warming device may include a heating element, a power source, and a controller. The heating element may comprise a conductive ink disposed on a substrate. The controllable thermal warming device may be used in any suitable manner as part of a heating system to heat any suitable matter, including, for example, blankets, clothing, consumer products, farming products, apparel, restaurant products, HVAC products, building construction products, hospital and other medical products, vehicles, to name a few.

DETAILED DESCRIPTION

Figure 1:
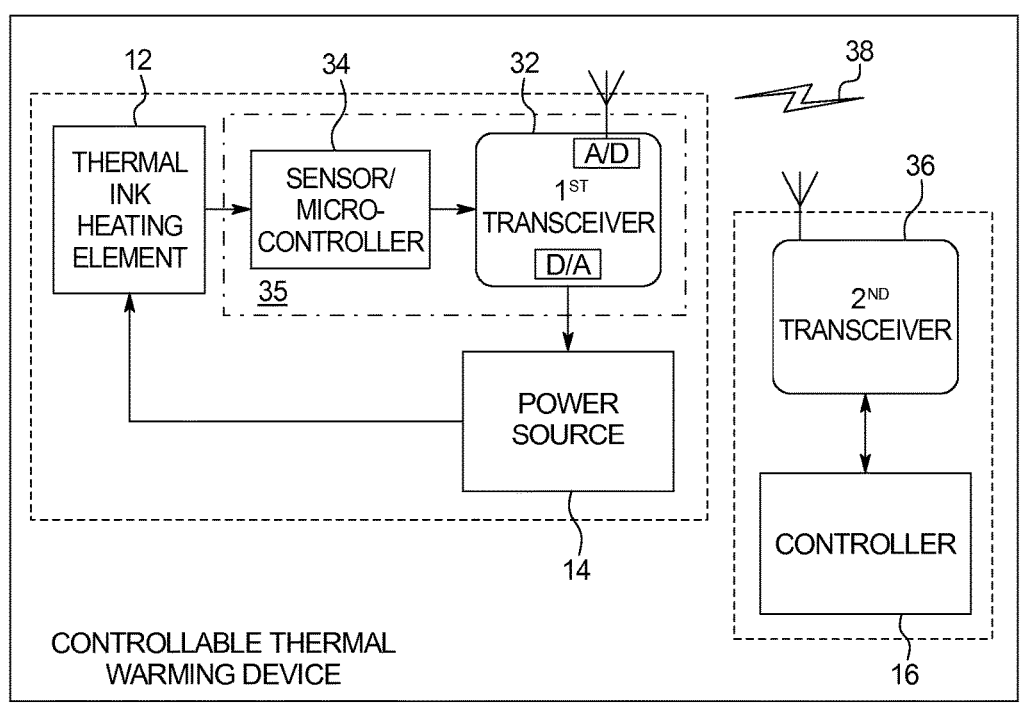
FIG. 1 is a functional block diagram of a controllable thermal warming device including a radio frequency link in accordance with an embodiment of the disclosure.

While the present disclosure may be susceptible to embodiment in different forms, there is shown in the drawings, and will be described herein in detail, one or more embodiments with the understanding that the present description is to be considered an exemplification of the principles of the disclosure and is not intended to be exhaustive or to limit the disclosure to the details of construction and the arrangements of components set forth in the following description or illustrated in the drawings.

FIG. 1 is a functional block diagram of a controllable thermal warming device 10 in accordance with an embodiment of the invention. In accordance with the embodiment of FIG. 1, the controllable thermal warming device 10 includes a heating element in the form of a thermal ink heating element 12 configured to generate or otherwise radiate heat, a power source 14 coupled to the thermal ink heating element 12 and adapted to provide a voltage to the thermal ink heating element 12, and a controller 16 coupled to the power source 14 and the thermal ink heating element 12. The heating element 12, the power source 14 and the controller 16 may have any suitable construction and include any suitable features. The controller 16 may, for example, include a memory and a processor coupled to the memory, or elements associated with an electromechanical controller. Among other things, as described below, the controller 16 may be adapted to control the voltage delivered to the thermal ink heating element 12 and to detect an operating characteristic (e.g., a current, a resistance, a temperature, etc.) of the thermal ink heating element 12 and, in response to the characteristic, adjust the voltage delivered to the thermal ink heating element 12.

The controllable thermal warming device 10 is configured to be activated or otherwise controllable by radio frequency signal in any suitable manner, and in this regard may include one or more radio frequency (RF) link(s) to enable remote monitoring and control of the thermal ink heating element 12 during operation. The controller 16 may be activated or otherwise controlled by radio frequency signal. FIG. 1 provides an example of the controllable thermal warming device 10 in accordance with an embodiment of the disclosure, which is adapted to control the controller 16 from a location remote to the thermal ink heating element 12, to (1) cause, or otherwise control, the delivery of voltage to the thermal ink heating element 12, (2) to detect an operating characteristic of the thermal ink heating element 12 and, (3) in response to the characteristic, to adjust the voltage delivered to the thermal ink heating element 12.

The controllable thermal warming device 10 of FIG. 1 includes the thermal ink heating element 12, the power source 14 coupled to the thermal ink heating element 12, and a first transceiver 32 operatively coupled to the power source 14 and the thermal ink heating element 12. An optional sensor/microcontroller 34 may also be included to detect a characteristic(s) of the thermal ink heating element 12 and/or control operation of the first transceiver 32. The controller 16, remotely located from the thermal ink heating element 12 and the power source 14, is coupled to a second transceiver 38. The controller 16 is therefore operatively coupled to the power source 14 via the first and second transceivers 32, 36 communicating via an RF link 38.

The first and second transceivers 32,36 may be one of any number of types of suitable transceivers configured to communicate using one of any number of radio frequency, or wireless link protocols. For example, for short range applications up to 10 yards, the first and second transceiver 32, 36 may be Bluetooth™ transceivers capable of transmitting and receiving over the RF link 38 using one of a number of versions of the Institute of Electrical and Electronic Engineers, Inc. (IEEE) 802.15 protocols. Using the current version (version 1.2) of IEEE 802.15, the controller 16 can remotely monitor and control up to eight separate thermal ink heating elements 12 via the second transceiver 36 (without additional power amplification). In that case, the second transceiver 36 establishes a Bluetooth™ "piconet" with the first transceiver 32 and possibly seven other like transceivers. The individual RF link 38 between each first transceiver 32 and the second transceiver 36 allows each first transceiver 32 to transmit operation characteristic data about its thermal ink heating element 12 to the second transceiver 36 and allows the second transceiver 36 to transmit operation characteristic adjustment data to each of the first transceivers 32 for use by the power source 14. Thus, the controller 16 and second transceiver 36 located in a nurses station may concurrently monitor and control the temperature of thermal ink heated blankets of eight patients located in a recovery room. Such a Bluetooth™ piconet may be further linked together with other Bluetooth™ piconets to form a large wireless monitoring and control network.

When using a Bluetooth™ protocol, the microcontroller of the sensor/microcontroller 34 is configured with a Bluetooth™ microcontroller and suitable Bluetooth™ control logic, optionally formed as a single chipset. Although not separately illustrated, the second transceiver 36 is similarly configured with a Bluetooth™ microcontroller and suitable Bluetooth™ control logic, formed as a single chipset. If any wireless link protocol requiring digital signal transmission is utilized, signals representing operating characteristics of the thermal ink heating element 12 may be converted to digital signals suitable for transmission via an analog-to-digital (A/D) converter in the 1st transceiver 32, and vice versa.

For low power applications requiring monitoring and control of tens, hundreds or even thousands of thermal ink heating elements 12 per second transceiver 36, the first and second transceiver 32, 36 may be configured as Zigbee transceivers capable of transmitting and receiving over an RF link using IEEE 802.15.4 protocol. In that case, the first transceiver 32 and the sensor/microcontroller 34 are combined to form a "ZigBee sensor" 35 that performs the sensor and transmit function and includes a Zigbee specific microcontroller. Similarly, the second transceiver 36 also includes a ZigBee specific microcontroller (not separately illustrated) to form a second ZigBee sensor. A single Z-link ZigBee chipset available from Atmel® Corporation may be utilized for this purpose.

Operating much like a Bluetooth™ piconet, the second transceiver 36 (and its associated ZigBee microcontroller) acts as a "network coordinator" to link the first transceiver(s) 32 to the second transceiver 36 to form a "ZigBee monitoring network". A large number of ZigBee sensors (i.e., the first transceiver 32 and associated microcontroller and sensor) communicating with each other and the network coordinator (i.e., the second transceiver 36 and associated microcontroller) may be formed, with one ZigBee sensor per thermal ink heating element 12. Monitored operating characteristics of the thermal ink heating elements) 12 can then be transmitted from the first ZigBee sensor 35 directly to the second transceiver 36 (network coordinator), or from the first ZigBee sensor 35 to one of any number of other ZigBee sensors in the ZigBee monitoring network, in a relay fashion, to the second transceiver 36 (network coordinator), and then to the controller 16. In this way, the controller 16 can monitor the selected operating characteristic(s) of the thermal ink heating element 12, and if necessary, cause associated adjustments to the voltage delivered by the power source 14 to the thermal ink heating element 12.

Although not separately illustrated, it is contemplated that future generations of one or more "micro" ZigBee sensors may be embedded directly into or onto the piece of clothing, the pouch, the blanket, the mirror, the hospital cover, etc. housing the thermal ink heating element 12.

For even longer range applications requiring monitoring and control of many thermal ink heating elements 12 per second transceiver 36, the first and second transceiver 32, 36 may be configured as WiFi transceivers capable of transmitting and receiving over the RF link 38 using IEEE 802.11a, 802.11b, or 802.11g protocols, depending on the frequency selected (e.g., 2.4 GHz range, 5 GHz range). Like the Bluetooth and ZigBee examples described above, the microcontroller of the sensor/microcontroller 34 is configured with a WiFi specific microcontroller. Additionally, however, each of the individual WiFi microcontrollers (and therefore each of the thermal ink heating elements 12) is operatively coupled to a computer having a WiFi specific transceiver installed therein (i.e., the first transceiver 32). The individual WiFi microcontrollers may be operatively coupled to the computer/WiFi transceiver via a wire line, another RF link such as, for example, an Infrared (IR) link or a cellular mobile station link (e.g., GSM, CDMA, TDMA), or a combination thereof. Thus, using such a WiFi "mesh network", and an Internet capable controller 16 (e.g., personal computer), monitoring may be accomplished from any location having access to the Internet. For example, a manufacturer of polymeric-based landfill liners desiring to maintain a relatively constant warm temperature during the curing process of a 700 square foot liner during the curing process, may utilize hundreds of thermal ink heating elements 12 arranged in a WiFi mesh network to monitor temperatures via a remotely located personal computer.

Although not separately illustrated, each of the first and second transceivers 32, 36 configured in one of any number of suitable wireless communication protocols, may further include one or more power or control buttons, and/or one or more visual or audible indicators to assist an individual. For example, if the first and second transceivers 32, 36 are configured using a Bluetooth protocol, the second transceiver 36 may include an Acquire button and a light emitting diode (LED) where the actuation of the Acquire button initiates formation of the piconet and where the LED indicates successful acquisition of the first transceiver 32 into the piconet.

Generally, during operation, the thermal ink heating element 12 radiates heat in response to a current generated in the thermal ink heating element 12 by application of the voltage from the power source 14. As the voltage is increased, the current increases. As the current increases, the resistance increases, and resulting heat is generated. With increased resistance, more voltage is needed to maintain the same current (and therefore temperature). Accordingly, using one or more of the operating characteristics of the thermal ink heating element 12 such as, for example, resistance, temperature, current, etc., the controller 16 makes adjustments to the voltage delivered by the power source 14. Thus, the feedback arrangement of the thermal ink heating element 12, the controller 16, and the power source 14 enables the temperature of the heat radiating from the thermal ink heating element 12 to be maintained at a relatively steady temperature; in this case, about 100 degrees Fahrenheit.

Figure 2:
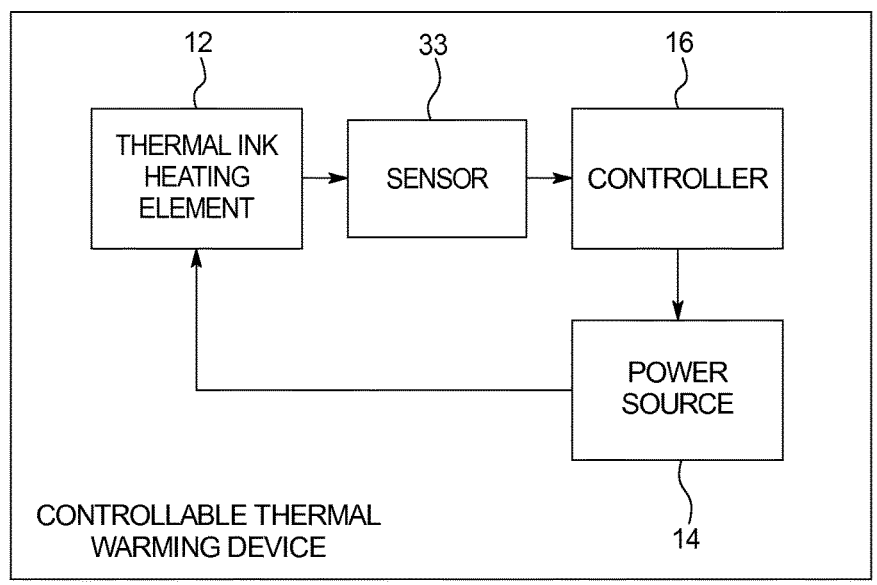
FIG. 2 is a functional block diagram of another controllable thermal warming device in accordance with an other embodiment of the disclosure.

FIG. 2 is a functional block diagram of another controllable thermal warming device 19 that includes a sensor 33 in accordance with an embodiment of the invention. As illustrated in FIG. 2, the controllable thermal warming device 19 includes the thermal ink heating element 12 configured to generate heat, the power source 14 coupled to the thermal ink heating element 12 and adapted to provide a voltage to the thermal ink heating element 12, the controller 16 coupled to the power source 14, and the sensor 33 coupled between the thermal ink heating element 12 and the controller 16. In this feedback arrangement, the sensor 33 is adapted to detect an operating characteristic of the thermal ink heating element 12 (e.g., a temperature) and transmit the operating characteristic to the controller 16. In response to receiving the operating characteristic, the controller 16 causes an adjustment to the voltage delivered to the thermal ink heating element 12. The controllable thermal warming device 19 may include any suitable means for activating or otherwise controlling the controller 16 by radio frequency.

Figure 3:
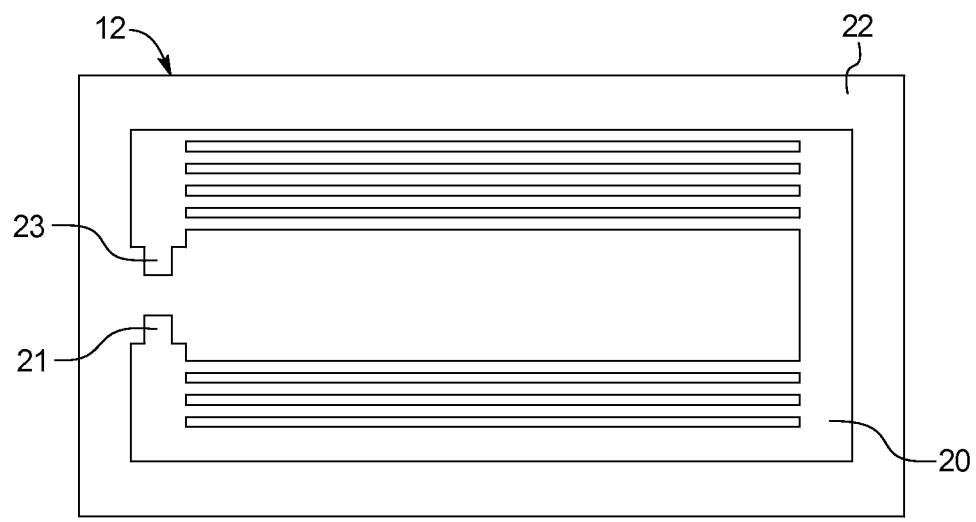
FIG. 3 is a top view of a thermal ink heating element in accordance with an embodiment of the disclosure.

Referring to FIGS. 1 and 2, the thermal ink heating element 12 may have any suitable configuration and structure. For example, FIG. 3 is a top view of an exemplary thermal ink heating element 12. In the illustrated example, the thermal ink heating element 12 includes a conductive ink 20 fixedly disposed on a substrate 22. The conductive ink 20 includes a first conductive ink pad 21 and a second conductive ink pad 23. The conductive ink 20 may be an ultra violet (UV) ink, for example, FD 3500 CL UV ink made by Allied Photochemical of Kimball, Mich., or any other suitable conductive ink. The substrate 22 may be one of any number of materials, such as, for example, acetate, Mylar, Liquiflex, paper or cloth and may have any suitable construction and configuration.

Figure 20:
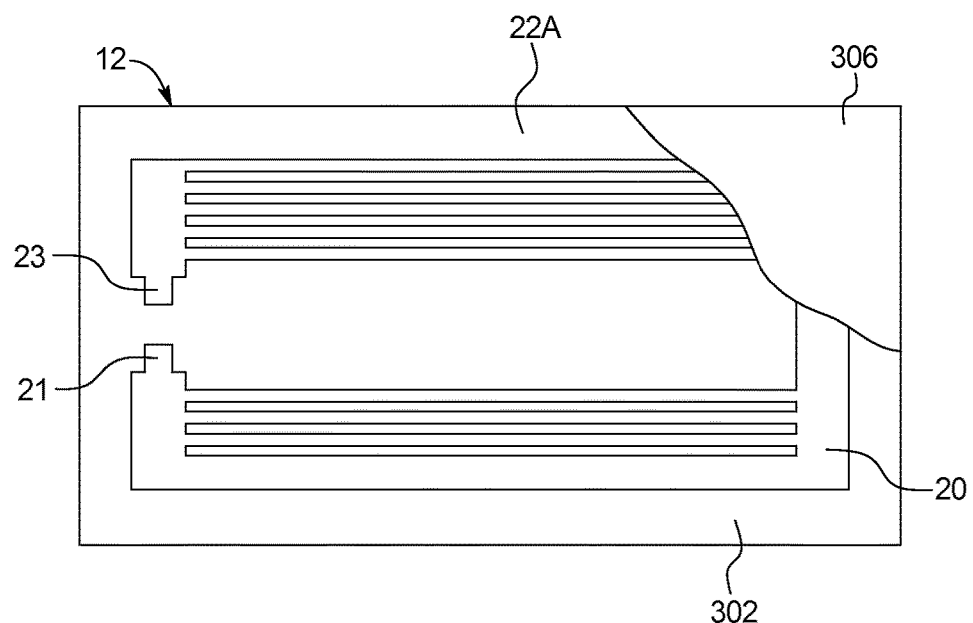
FIG. 20 is a top plan view of a thermal ink heating element and a release layer removably affixed to the film in accordance with another embodiment of the disclosure, the thermal ink heating element shown in broken view to illustrate the release layer.

In accordance with other embodiments, the thermal ink heating element 12 may be releasably or otherwise removably securable to an other structure so that the thermal ink heating element may be used on a wider variety of items, such as, for example, disposable or reusable items. The thermal ink heating 12 element may, for example, be removably secured to disposable hospital gowns or on other clothing, any consumer products or building structure, or any other suitable structure. The manner of removably securing the thermal heating element to such other structure may be accomplished in any suitable manner. Referring to FIG. 20, for example, the substrate 22A of the thermal ink heating element 12 may be constructed of a material that includes a film 302 comprising mylar or other suitable material. An adhesive is affixed to a backside of the film 302 and a removable release layer 306 is affixed to the film for removably securing the film to other structure. The thermal ink heating element 12 may be releasably secured to the structure with the adhesive after removal of the release layer 306. The substrate 22A may, for example, be a pressure sensitive film commercially available from FLEXCON of Spencer, Mass. or any similar product. In accordance with other embodiments, any suitable strip for adhering or other suitable material such as any suitable two-sided tape, tape adhesive, adhesive backing, glue, hook and loop fastening means or other suitable material, utilized with or without a release layer, may be applied to the thermal ink heating element 12 to facilitate removable securement of the thermal ink heating element to the structure.

The conductive ink 20 is fixedly disposed on the substrate 22 using any suitable manner such as, for example, affixing the conductive ink 20 onto the substrate 22 via a conventional printing press or via a screen printing press. The process of affixing the conductive ink 20 to the substrate 22 may begin by creating a pattern. The pattern may include a series of lines and be created with the aid of a computer and a computer aided drawing program. Once created, the pattern may be used to generate a film positive which is then translated into a screen, stencil, printing plate, or the like. Utilizing, for example, the stencil, the conductive ink 20 may be applied to the substrate 22 either by hand or automatically via a printing press. After application to the substrate 22, the conductive ink 20 is cured and set via application of a UV light, thereby forming the thermal ink heating element 12.

Figure 4:
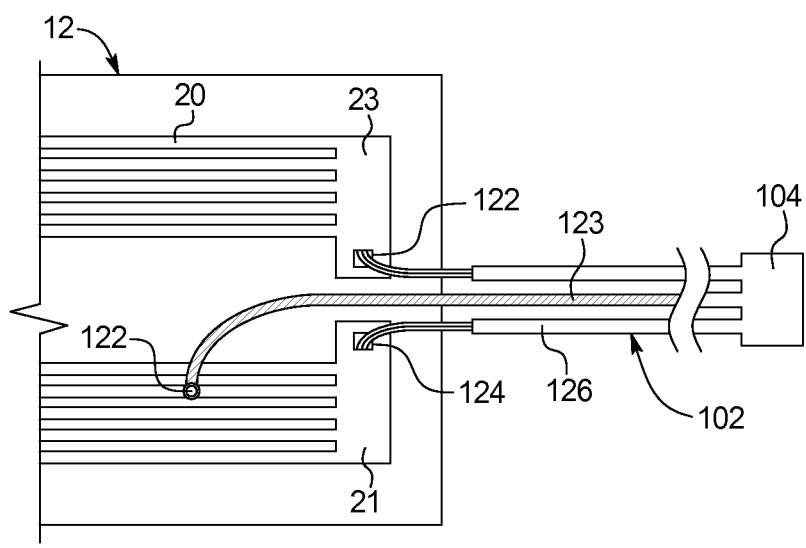
FIG. 4 is a top view of another thermal ink heating element including a sensor in accordance with an embodiment of the disclosure.

FIG. 4 is a top view of another exemplary thermal ink heating element fixedly coupled to, inter alia, a sensor in accordance with an embodiment of the invention. In the illustrated example, the sensor is configured as a thermally sensitive resistor. Additional details of the thermally sensitive resistor are discussed below in connection to FIG. 5.

Referring again to FIG. 3, once formed, the thermal ink heating element 12, with or without the sensor 33, may be used in a wide variety of heating system applications. For example, the thermal ink heating element 12 may be inserted into or onto a piece of clothing, a pouch, a blanket, a mirror, a hospital cover, etc. A wide variety of applications for the thermal ink heating element 12 are described hereinafter and in U.S. patent application Ser. No. 10/115,846 filed Apr. 3, 2002, and in an associated U.S. continuation-in-part patent application Ser. No. 10/854,838 filed May 27, 2004, both naming Haas et al. as inventors, and herein incorporated by reference in their entirety.

In the controllable thermal warming devices 10,19 illustrated by the functional block diagrams of FIGS. 1 and 2, elements such as the power source 14, the thermal ink heating element 12, the controller 16 and the sensor 33 may be connected via a wire line scheme.

As mentioned above, the controllable thermal warming devices 10 and 19 include the thermal ink heating element 12, the controller 16 and the power source 14 in a feedback control arrangement. When enabled, it is contemplated that the controllable thermal warming device 10 may include additional components such as sensors, transceivers, connectors, plugs, buttons, etc.

Figure 5:
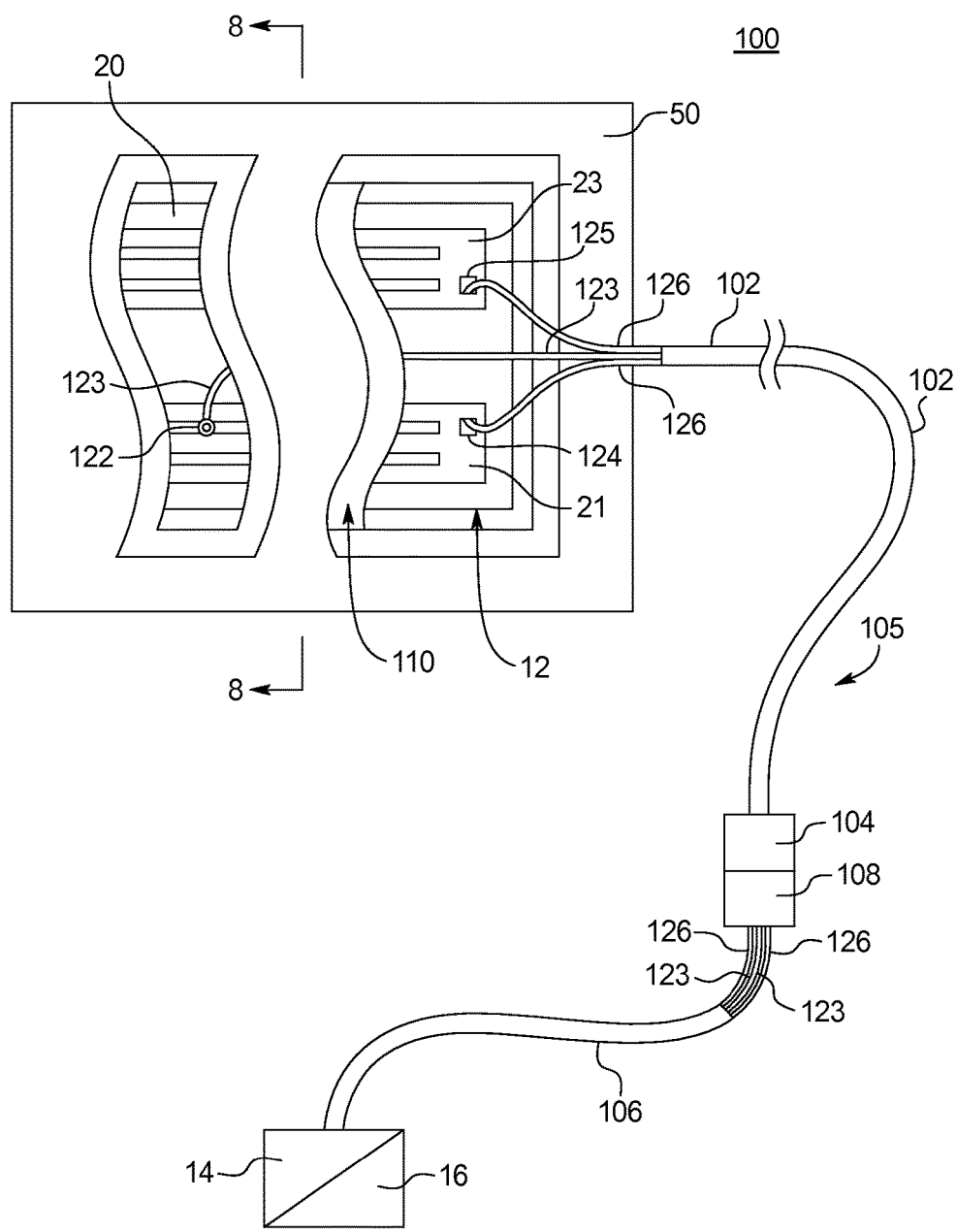
FIG. 5 is a top plan view of the thermal ink heating element of FIG. 4 in a pouch, the pouch being shown in broken view.

For example, FIG. 5 is a top plan view of a controllable thermal warming device 100 having a sensor in accordance with an embodiment of the invention. The controllable thermal warming device 100 includes the thermal ink heating element 12 configured to generate heat, the power source 14 operatively coupled to the thermal ink heating element 12 via a wire link 105, and the controller 16 operatively coupled to the thermal ink heating element 12 and the power source 14. In the illustrated example, the wire link 105 includes a temperature controller connector 102 coupled to the thermal ink heating element 12 and terminating in a first socket 104. The wire link 105 also includes a temperature cable 106 coupled to the controller 16 and the power source 14 and terminating in a second socket 108. The first and second sockets 104, 108 are mated to provide a continuous electrical path between the power source 14 and the thermal ink heating element 12, and to provide a continuous signal path from the sensor coupled to the thermal ink heating element 12 to the controller 16. Although illustrated as an individual block, it is contemplated that the power supply 14 and the controller 16 may be illustrated as separate blocks configured to maintain the feedback control path.

The power source 14 of FIG. 5 is may, for example, be either a single or dual Ni-MH battery pack, made by AVT, Inc., and integrated with the controller 16. Each individual pack may consist of twelve +1.2 volt cells in series to yield an overall voltage of +14.4 VDC rated at 6.8 amp-hour. Typically, if a single Ni-MH battery pack is used in conjunction with the thermal ink heating element 12, 8-10 hours of voltage delivery time is yielded. If a dual Ni-MH battery pack is used conjunction with the thermal ink heating element 12, 14-16 hours can be yielded. Although described above in terms of providing a DC voltage output, it is contemplated that the power source 14 may be one of any number of suitable power sources. For example, the power source 14 may be a DC power source, an AC power source, a solar power source, or one of any number of other power sources that may be able to provide a direct current flow in the thermal ink heating element 12.

The power source 14 of FIG. 5 may be also configured using battery packs requiring use of a battery charger, such as, for example, a Model DV2005S1Series battery charger manufactured by Texas Instruments, Inc. The battery charger is adapted to receive its power from a boost converter that steps up the voltage output of the internal power supply. The higher voltage output is required to properly charge a twelve cell battery pack. The battery charger also incorporates safety features that cause the charge cycle to be terminated in the event a maximum charge time and/or a maximum voltage exceeds a pre-set limit.

During operation, the power source 14, optionally integrated with the controller 16, is regulated by the controller 16 to deliver the appropriate voltage to the thermal ink heating element 12 in order to maintain a current that causes heat to be radiated at a temperature of approximately +100+/−4 degrees Fahrenheit. As described above in connection with FIG. 1, current flow in the thermal ink results when the free electrons of the thermal ink are repelled by the negative battery terminal of the power source 14. Heat is generated by the associated resistance of the flowing electrons in the conductive ink 20. The controller 16, electrically connected to the thermal ink heating element 12 via the temperature cable 106 and the temperature controller connector 102, receives temperature characteristics of the thermal ink heating element 12. Based on those temperature characteristics, the controller 16 regulates the voltage delivered by the power source 14 to the thermal ink heating element 12 to maintain the desired approximate +100 degrees Fahrenheit temperature.

In some cases, it may be useful to determine the capacity of the power source 14. The capacity of the power source 14 may be determined by measuring the voltage of the power source 14 and then displaying the results visually through use of a capacity meter. One example of such a capacity meter is a capacity meter having Part. No. 58-90001000-000, manufactured by WJH Engineering, and utilizing a National Semiconductor device (LM3419) designed to drive a series of five LEDs. The five LEDs indicate a FULL battery condition, a {fraction (%)} battery condition, a {fraction (%)} battery condition, a {fraction (%)} battery condition or an EMPTY battery condition. When coupled to the capacity meter, a drop in the capacity of the power source 14 below a minimum set threshold will cause an alarm to sound on the capacity meter. It should be noted that during operation, the capacity meter is electrically disconnected from the power source 14 when the controller 16 turns off the power source 14. This ensures that the battery packs do not inadvertently self-discharge.

As previously mentioned, the power source 14 may be configured using an AC power source. In that case, the controller 16 may contain a switching power supply that is capable of operating from 85 to 250 VAC at a rated output of 15 VDC @ 7 amps. The switching power supply also provides the power to charge the internal battery pack(s). It is further contemplated that the power source 14 may also be configured using another type of power source 14 such as a +12 to +16 VDC source from a vehicle cigarette lighter or from a DC source within an emergency vehicle.

Figure 6:
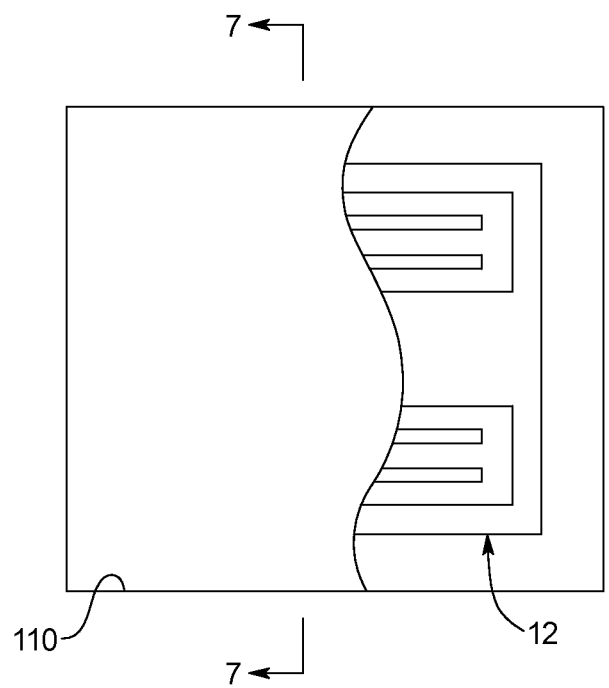
FIG. 6 is a top plan view of the thermal ink heating element of FIG. 3 in the pouch, the pouch being shown in broken view.
Figure 8:
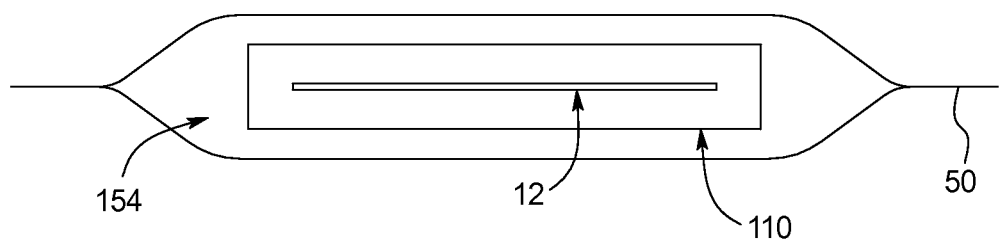
FIG. 8 is a section view taken along lines 8-8 in FIG. 5.
Figure 10:
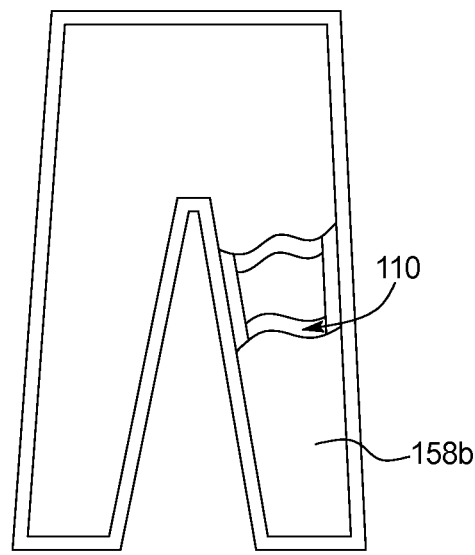
FIG. 10 is a plan view of an exemplary pants garment that includes the thermal ink heating element of FIG. 3.
Figure 11:
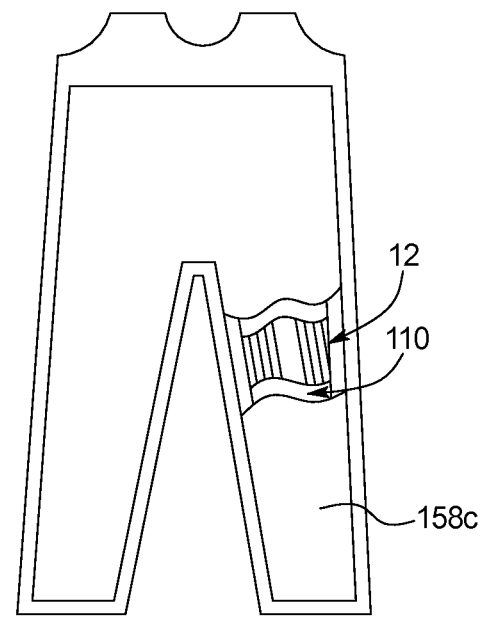
FIG. 11 is a plan view of another exemplary pants garment that includes the thermal ink heating element of FIG. 3.
Figure 12:
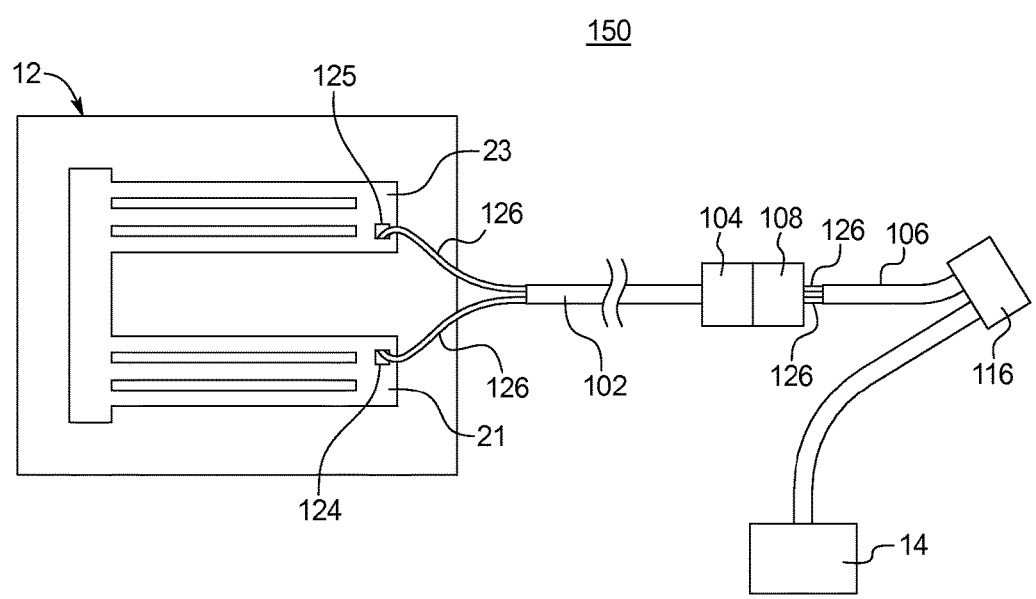
FIG. 12 is a top plan view of another controllable thermal warming device in accordance with another embodiment of the disclosure.

For ease of use, the thermal ink heating element 12 is fixedly coupled to the temperature controller connector 102 and placed in a pouch 110. For example, FIG. 6 is a top plan view of the thermal ink heating element of FIG. 3 in a pouch, the pouch being shown in broken view, and FIG. 8 is a section view taken along the line 8-8 in FIG. 6. The pouch 110 may then be hermetically sealed and the pouch/thermal ink heating element combination placed in a blanket 50, garment, or the like. For example, FIG. 8 is a section view taken along lines 9-9 in FIG. 5 showing the thermal ink heating element 12 inside the pouch 110 inside the blanket 50. FIGS. 10-12, are views of exemplary garments that include the controllable thermal warming device of FIG. 6.

After use, the pouch/thermal ink heating element combination can be removed from the blanket and then the thermal ink heating element 12 and its associated the temperature controller connector 102 can be removed from the pouch 110 for reuse in a new pouch. The spent pouch 110 and/or blanket 50 may then be disposed of.

Also as previously mentioned, the controller 16 preferably causes the thermal ink heating element 12 to maintain its heat output at +100 degrees Fahrenheit, +/−4 degrees. Alternatively, the controller 16 may be configured to causes the thermal ink heating element 12 to maintain the heat output of its associated blanket or garment at +100 degrees Fahrenheit, +/−4 degrees.

The controller 16 of FIG. 5 includes a proportional integral derivative (PID) controller, a control sensor such as a thermistor coupled to the thermal ink heating element 12, and one or more safety devices. For example, the controller 16 of FIG. 5 may include a PID controller having Part. No. 5C7-362, manufactured by Oven Industries, Inc., and capable of operating in P, PI, PD or PID control. Such a PID controller is adapted to enable the thermal ink heating element 12 to initially heat to +100 degrees Fahrenheit within 2 minutes, with subsequent heatings likely occurring in less time.

Such a PID controller is programmable via an RS232 communication port adapted for direct interface to a compatible PC and can therefore be coupled to a PC via a variety of communication cables having lengths commensurate with RS232 interface specifications. The RS 232 communications interface includes a 1500 VAC isolation from other electronic circuitry to minimize possible interferences due to noise or errant signals caused by common ground loops. When coupled to the PC, parameters of the PID controller may be set to desired values via the PC. Upon establishment of the parameters, the PC may be disconnected and the desired parameter settings retained in nonvolatile memory of the PID controller.

During operation utilizing the aforementioned PID controller, the output signal from the controller 16 (i.e., the PID controller) to the thermal ink heating element 12 is Pulse Width Modulated (PCM) and is PC selectable for either 675 Hz or 2700 Hz operation. Such a PCM scheme averages the amount of energy provided to the thermal ink heating element 12 and reduces extreme temperature excursions possible in an "on/off" system. As a result, the life and reliability of the power source 14 may be extended. In addition, such a PWM control scheme may afford control accuracy to within +/−0.05 degrees Celsius at the control sensor.

The controller 16 of FIG. 5 may utilize information provided by a sensor such as, for example, a thermally sensitive resistor or a thermistor 122, to cause the controller 16 to make subsequent adjustments to the voltage supplied to the thermal ink heating element. The thermistor 122, or control sensor is may be a Negative Temperature Coefficient (NTC) thermistor, rated at 15,000 ohms at +25 degrees Celsius, manufactured by Panasonic, Inc. and having part number ERT-D2FHL153S. For optimum accuracy of temperature control, the thermistor 122 is affixed directly to the thermal ink heating element 12. Alternatively, the thermistor 122 may be attached to a covering, for example, the pouch 110.

The controllable thermal warming device 100 may incorporate several safety devices and indications to protect the patient from potential injury. For example, if the temperature of the thermal ink heating element 12 climbs above +104 degree Fahrenheit, the controller 16 may automatically shut off the power to thermal ink heating element 12 and cause an alarm to sound. Such an alarm, for example an alarm having Part Number BRP2212L-12-C and manufactured by International Component, can be programmed to any upper limit and can be reset by the temperature controller 130. Similarly, the controller 16 can also cause a visual indication when the temperature of the thermal ink heating element 12 falls below +98 degree Fahrenheit or when the temperature of the thermal ink heating element 12 is within a programmable target window. The controller 16 may also be configured to cause an alarm to sound if the temperature cable 106 becomes disconnected from the temperature controller connector 102 or if the thermistor 122 is at fault and becomes shorted or opened.

The controller 16 may be coupled to the thermal ink heating element 12 using one of any number of methods, depending on the application selected for the thermal ink heating element 12. For example, in various medical applications, the temperature of the thermal ink heating element 12 should be automatically regulated to remain within +100+/−4 degree Fahrenheit. In other applications, an individual user may desire to manually control the temperature of the thermal ink heating element 12 to vary the temperature between +100 and +110 degree F. In this case, the controller 16 may be configured in an alternate fashion to enable manual adjustment by a user (described below).

Referring again to automatic temperature control of the thermal ink heating element 12 by the controller 16 of FIG. 5, the temperature controller connector 102 attaches to the thermal ink heating element 12, and includes heater element wires 126, the thermistor 122, a thermistor wire(s) 123, a first heater element contact pad 124, a second heater element contact pad 125, and the first socket 104. Each of the heater element wires 126 is an 18 gauge wire. As illustrated, one of the heater element wires 126 contacts the first heater element contact pad 124 and the other heater element wire 126 contacts the second heater element contact pad 125. The first and second heater element contact pads 124 and 125 are constructed of copper squares. Alternatively, the first and second heater element contact pads 124 and 125 may be constructed of another suitable conductive material. Also as illustrated, each of the first and second heater element contact pads 124 and 125 contacts the first and second conductive inks pads 21 and 23, respectively. Alternatively, each of the first and second heater element contact pads 124 and 125 may contact the conductive ink 20 at another location. It is contemplated that tape, copper rivets, conductive epoxy or any other suitable structure may be used to affix the heater element contact pads 124, 125 to the thermal ink heating element 12.

The thermistor wire(s) 123 is soldered to the thermistor 122 and adhesive tape used to affix the thermistor 122 to the thermal ink heating element 12. After connecting the temperature controller connector 102 to the thermal ink heating element 12, the first and second sockets 104, 108, respectively, may be mated, thereby coupling temperature cable 106 to the temperature controller connector 102. In the illustrated example of FIG. 5, the temperature cable 106 includes the second socket 134 and four wires; two of the wires comprise the heater element wires 126 and two of the wires comprise the thermistor wire(s) 123. Thus, the power source 14 is electrically connected to the conductive ink 20 and voltage is supplied from the power source 14 to the conductive ink 20 via the heating element wires 126. In addition, the controller 16 is coupled to the thermistor 122 via the thermistor wire(s) 123, thereby proving a feedback path to the controller 16. Utilizing operating information from the thermistor 122 (e.g., electrical resistance indicative of a temperature), the controller 16 controls the power source 14 via regulating the amount of voltage supplied to the conductive ink 20.

In an alternate embodiment, the thermistor 122 and associated thermistor wire(s) 123 may be deleted and the 18 gauge heating element wires 126 replaced by 22 gauge heating element wires 126. In that case, the PID controller may be replaced by an alternate controller allowing manual control of the temperature. For example, FIG. 12 is a top plan view of another controllable thermal warming device 150, in accordance with an embodiment of the invention. In the illustrated example of FIG. 12, the controller 16 has been replaced by an alternate controller 116, or a potentiometer assembly, having a solid state switch (MOSFET), a stable timer (NE555), a voltage comparator (LM393), a battery connector, a heating element connector and a control potentiometer with a built in On/Off switch.

During operation and after tactilely sensing the warmth of the thermal ink heating element 12, a user may cause the temperature of the thermal ink heating element 12 to be adjusted to a desired comfort level by manually adjusting a control knob within the alternate controller 116. The alternate controller 116 thereby enables the individual to regulate the amount of voltage supplied by the power source 14 to the conductive ink 20.

In summary, the basic design principle of the alternate controller 116 is to turn the solid state switch on and off very quickly and vary the voltage supplied to the conductive ink 20 by changing the ratio of the "On" time to "Off" time. The ratio is adjustable from 0% (completely turned off) to 100% (completely turned on) via the control potentiometer which can be adjusted to vary the input to the voltage comparator. The variable input voltage is then compared against the output voltage of the timer. Each time the voltage output of the timer crosses the threshold of the comparator, the output of the controller turns on and then back off. The frequency of this On/Off cycle is preferably selected to be approximately 300 Hz.

Figure 9:
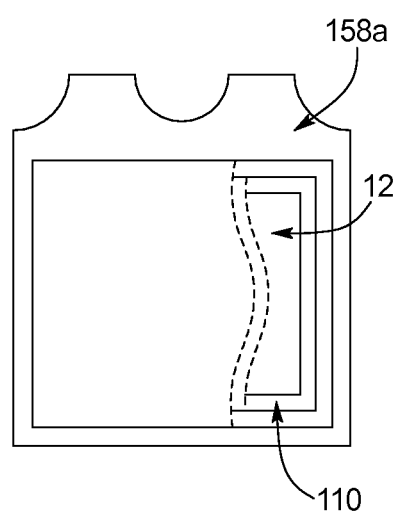
FIG. 9 is a plan view of an exemplary vest garment that includes the thermal ink heating element of FIG. 3.

The alternate controller 116 is configured to control the power source 14, that may be a battery such as, for example, a lithium ion battery or a nickel metal hydride type rechargeable battery, made by AVT, Inc. A battery charger, such as for example, a TM. Model MHTX-7 Series manufactured by XENOTRONIX, Inc., may be used to recharge the battery of FIG. 9. Alternatively, the power source 14 of the controllable thermal warming device 150 may be configured as a DC source when it is available. In addition, the alternate temperature controller 116 is capable of operating via a +12 to +16 VDC source provided by a vehicle cigarette lighter or via a DC source within an emergency vehicle.

The controller 16 or controller 116 may be eliminated in accordance with other embodiments. For example, there may not be a need to utilize a controller if the temperature of the thermal ink heating element 12 does not need to be closely controlled. Moreover, the heat dissipated by the thermal ink heating element 12 may be held constant by controlling the resistance of the thermal ink heating element 12 in accordance with such embodiments. The resistance of the thermal ink heating element 12 may be controlled in any suitable manner such as, for example, by adjusting the amount of conductive ink that is applied during the manufacturing process. With such an embodiment, the amount of heat developed through the element will be proportional to the voltage applied and the current drawn from the battery source as shown below:

Power(Heat dissipated)=Battery Voltage×Current Drawn where: Current Drawn=Battery Voltage/Heating Element Resistance.

The higher the resistance of the thermal ink heating element 12 the lower the operating temperature will be. As the resistance is decreased, the temperature of the thermal ink heating element 12 can be increased in a controlled manner. The temperature of the thermal ink heating element 12 may be controllable within certain ranges by maintaining a constant thermal ink heating element resistance.

Figure 13:
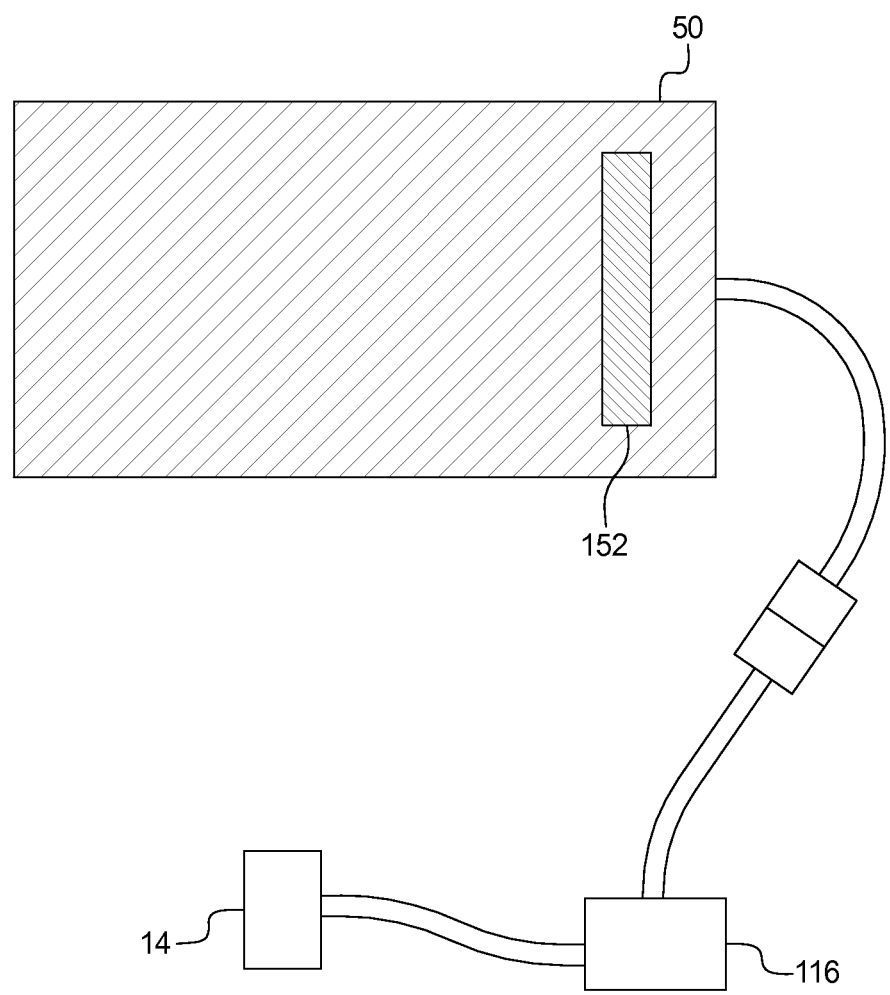
FIG. 13 is a top plan view of yet another controllable thermal warming device similar to the controllable thermal warming device of FIG. 6.

Like the controllable thermal warming device 100 described in connection with FIG. 5, the controllable thermal warming device 150 may be placed in a pouch 40. For example, FIG. 13 is a top plan view of the controllable thermal warming device 150 placed the blanket 50. The thermal ink heating element 12, with the temperature controller connector 102 attached, is first placed within the pouch 40, hermetically sealed, and the pouch/thermal ink heating element combination placed in a blanket 50 or the like.

Figure 14:
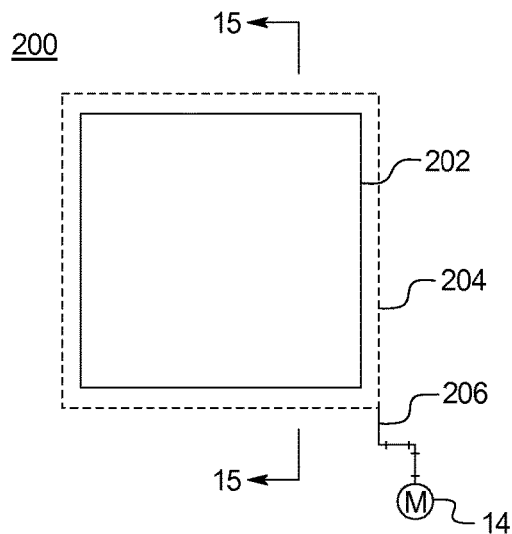
FIG. 14 is a front view of an exemplary glass panel assembly that includes the thermal ink heating element of FIG. 3.

Referring to FIGS. 13 and 14, the controllable thermal warming device 150 may be placed in a bore defined by the pouch 40 which, in turn, is placed in the blanket 50 or a covering 158 of a garment such as the vest or pants of FIGS. 10-12, as follows. A flap 152 in the blanket 50 is moved to an open position and the pouch 40, containing the controllable thermal warming device 150, is inserted through the pocket opening 152 and into a pocket cavity 154. The controllable thermal warming device 150 is then secured to the power source 14 with the cables extending from within the pocket cavity 154 to outside the pocket cavity 154. Activation of the power source 14 causes the controllable thermal warming device 150 to generate heat and warm all or portions of the blanket 50 or the garment. After the initial use, depending upon the construction of the controllable thermal warming device 150 and the extent of the initial use, the controllable thermal warming device 150 individually or in conjunction with the pouch 40 can be reused.

The covering 158 may be in one of any number of suitable forms, including, for example, in the form of apparel or clothing such as a vest (see, covering 158a of FIG. 9) or a pair of pants (see, covering 158fc of FIG. 10 and covering 158c of FIG. 11). The clothing may have any suitable outdoor or other use including, for example, clothing to be worn hunting, fishing, sporting, spectating, construction, or any other outdoor use, such as, for example, any use in connection with emergency, police, military, medical, traffic or similar uses. The size, location and number of pocket cavities 154 of the clothing figured to house the one or more controllable thermal warming devices 100 or 150 may vary. One or more controllable thermal warming devices may be included in any suitable garment and may used to heat any part of the body, including the torso, legs, arms, feet, hands, derriere or head.

Figure 15:
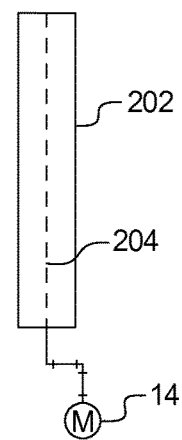
FIG. 15 is a section view taken along lines 15-15 in FIG. 14.

As mentioned above, thermal ink heating element 12 may be configured in one of any number of suitable patterns for use in one of any number of applications. For example, FIG. 14 is a front view of an exemplary glass panel 200 assembly utilizing a strip-shaped thermal ink heating element. The glass panel assembly 200 includes a glass plate 202 (e.g., a window, door, etc.) having an outer perimeter encased in a strip-shaped thermal ink heating element, or thermal ink heating strip 204. The thermal ink heating strip 204 utilizes the conductive ink 20 disposed on the substrate in a strip-shaped pattern. In addition, the power source 14 is coupled to the thermal ink heating strip 204 via a suitable power connection 206. FIG. 15 is a section view taken along lines 16-16 in FIG. 15.

Figure 16:
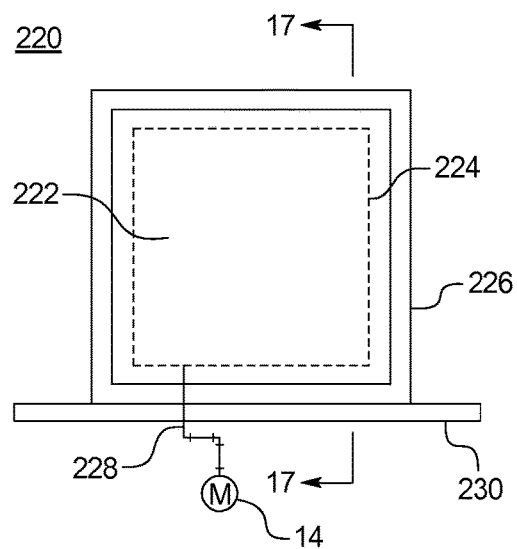
FIG. 16 is a front view of another exemplary glass panel assembly that includes a thermal ink heating element utilizing an invisible conductive ink.
Figure 17:
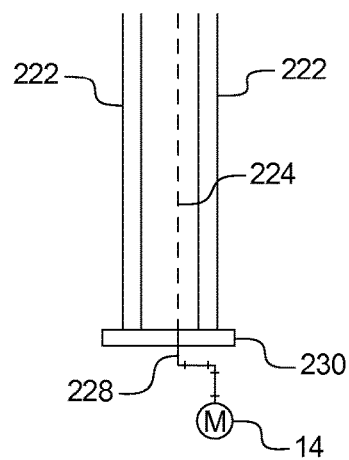
FIG. 17 is a section view taken along lines 17-17 in FIG. 16.

FIG. 16 is a front view of another exemplary glass panel assembly 220 that includes a sheet-shaped thermal ink heating element 224 sandwiched between two glass plates 222. In the illustrated example, the glass panel assembly 220 is configured in a window arrangement on a window sill 230, however, other arrangements are contemplated. The sheet-shaped thermal ink heating element 224 utilizes an invisible conductive ink, and may be placed directly against one of the two glass plates 222, or may be placed in a space between the two glass plates 222. The glass panel assembly 220 also includes the power source 14 coupled to the invisible conductive ink of the sheet-shaped thermal ink heating element 222 via a suitable power connection 228. FIG. 17 is a section view taken along lines 18-18 in FIG. 16.

Figure 7:
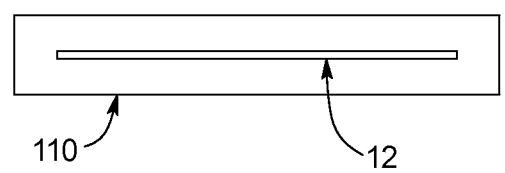
FIG. 7 is a section view taken along the line 7-7 in FIG. 6.
Figure 18:
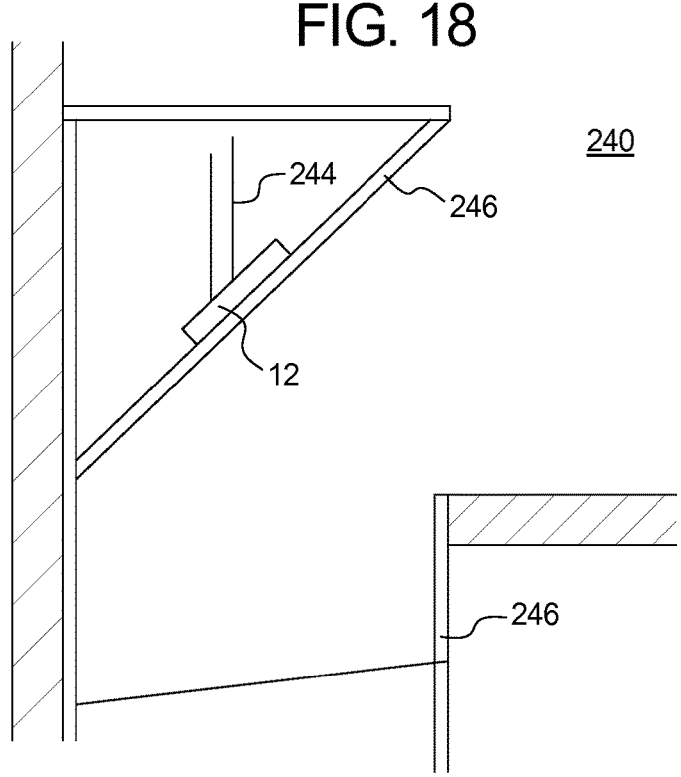
FIG. 18 is a side view of an exemplary building structure duct assembly that includes the thermal ink heating element of FIG. 3.
Figure 19:
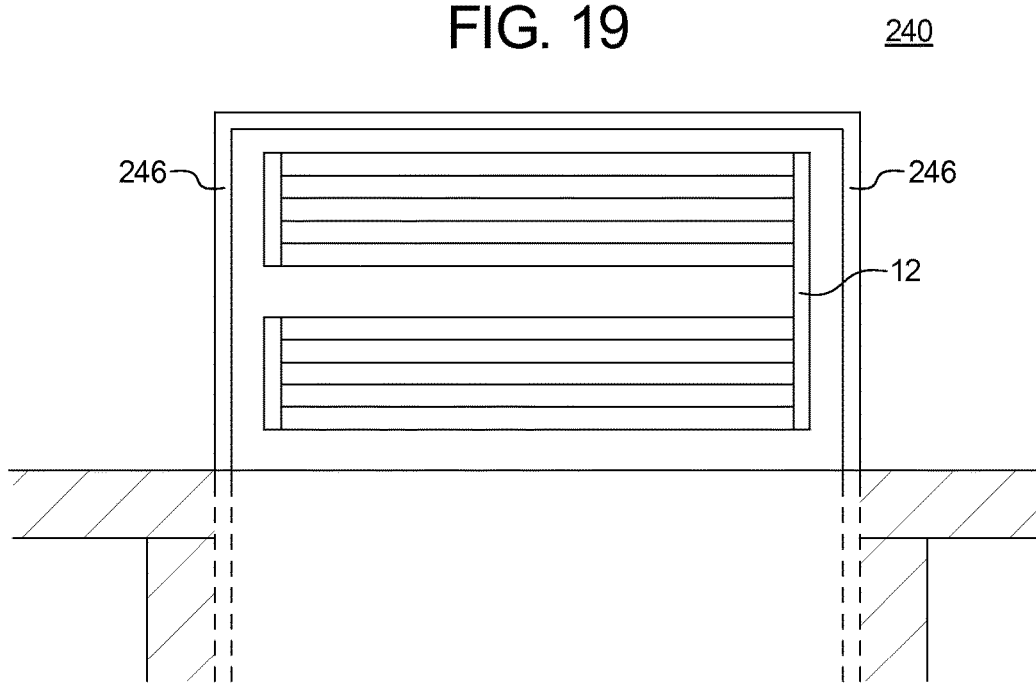
FIG. 19 is a front view of the exemplary building structure duct assembly of FIG. 18.

The thermal ink heating element 12 may also be adapted to warm ambient air temperature. For example, FIG. 18 is a side view of an exemplary duct assembly 240 that includes a thermal ink heating element, for example, the thermal ink heating element 12. The thermal ink heating element may be contained inside of a pouch, for example the pouch 110 (see, FIGS. 5-7), and may be coupled to the power source 14 via a power connection 244. As illustrated by FIG. 18, the heating element 12 is positioned between the duct work 246 of a building structure. A partial front view of the duct assembly 240 is shown in FIG. 19. A similar configuration may be utilized to warm floors and walls.

In addition to wearing apparel, blankets, glass windows, floors, and walls, the thermal ink heating element 12 may be configured to provide heat to any number of consumer products such as baby bottles, baby carriages, pet water bowls, pet accessories, ceiling fans, mirrors, beverage coolers offering heat, pool coverings, vehicle portions and accessories such as a vehicle battery, a vehicle window, a vehicle seat or a vehicle electronic element (e.g., a vehicle sensor, a vehicle micro-controller). The thermal ink heating element 12 may also be configured to provide heat to farming products or tools such as livestock water troughs, restaurant products and food, military troop gear such as sleeping bags, hospital and patient products, and vehicles such as law enforcement and fire/rescue vehicles. The thermal ink heating element 12 may also be utilized to melt snow on, for example, a sidewalk or driveway. Additional examples, too numerous to mention, are also contemplated.

As is apparent in the above discussion, each of the controllable thermal warming devices described herein may provide a lightweight, flexible, portable, reusable, and/or disposable controllable heating device for use in blankets, wearing apparel and the like.

While the concepts of the present disclosure have been illustrated and described in detail in the drawings and foregoing description, such an illustration and description is to be considered as exemplary and not restrictive in character, it being understood that only the illustrative embodiment has been shown and described and that all changes and modifications that come within the spirit of the disclosure are desired to be protected by the claims set forth below.

What is claimed is:

1. A portable heating system comprising a controllable thermal warming device, the controllable warming device comprising;
   a thermal heating element comprised of conductive inks printed in the form of a series of interconnected lines having a definite or definitive pattern and fixedly disposed on a single sheet of nonconductive substrate;
   a power source operatively coupled to the conductive ink pattern, the power source adapted to deliver a voltage to the conductive ink to cause the conductive ink pattern to radiate heat;
   a controller operatively coupled to the power source and the conductive ink, the controller adapted to control the voltage to the conductive ink pattern whereby the heating element, the power source and the controller comprise a portable unit.

2. The controllable thermal warming device of claim 1 wherein the heating element is comprised of a definite pattern containing a specific number, design, and configuration of lines so as to further control the evenness and out-put of heat.

3. The controllable thermal warming device of claim 1 wherein the controller is further adapted to detect an operating of the conductive ink pattern and adjusts the voltage in response to the operating characteristic.

4. The controllable thermal warming device of claim 3, wherein the operating characteristic is selected from the group consisting of an electrical resistance, a current, a voltage and a temperature.

5. The controllable thermal warming device of claim 1, further comprising a thermally sensitive resistor coupled to the conductive ink pattern and the controller, the thermally sensitive resistor adjusting an electrical resistance in response to detecting a temperature change in the heat radiated by the conductive ink pattern.

6. The controllable thermal warming device of claim 1, further comprising a negative temperature coefficient thermistor, the negative temperature coefficient thermistor decreasing an electrical resistance in response to an increase in the heat radiated by the conductive ink pattern.

7. The controllable thermal warming device of claim 3, wherein the controller means comprises' a proportional-integral-derivative controller adapted to adjust the voltage delivered from the power supply to maintain a pre-selected temperature range of the heat radiating from the conductive ink pattern.

8. The controllable thermal warming device of claim 3, wherein the controller comprises a potentiometer assembly, manual adjustment of the potentiometer assembly by a user of the controller thermal warming device adjusting the voltage delivered from the power source to cause a temperature change in the heat radiated by the conductive ink pattern.

9. The controllable thermal warming device of claim 3, wherein the controller comprises a processor and a memory coupled to the processor.

10. The controllable thermal warming device of claim 3, wherein the controller is fixedly coupled to the power source and the conductive ink pattern via a wire line link.

11. The controllable thermal warming device of claim 1, wherein the delivery and the control of the voltage delivered to the conductive ink pattern is achieved by a radio frequency signal.

12. The controllable thermal warming device of claim 11, wherein the radio frequency signal comprises a wireless networking system which includes a transmitter and a receiver electronically connected to the heating element.

13. The controllable thermal warming device of claim 11, further comprising a first transceiver electrically coupled to the conductive ink pattern and the power source; and a second transceiver electrically coupled to the controller, wherein the first and the second transceivers are adapted to transmit radio frequency signals.

14. The controllable thermal warming device of claim 11, wherein the radio frequency signal comprises short range, wireless, networking, communications systems.

15. The controllable thermal warming device of claim 1, further comprising a plurality of heating elements, the radio frequency means and controller configured to remotely control each of the heating elements.

16. The controllable thermal device of claim 1, wherein the substrate comprises a pressure sensitive film allowing for the transferability of the heating element to any number of surfaces or products.

17. The controllable thermal warming device of claim 1, wherein the device delivers controlled heat to a building structure element selected from the group consisting of a glass plate, a floor, a wall, a door, a mirror, a roof, a ceiling fan and a HVAC duct.

18. The controllable thermal warming device of claim 1, wherein the device delivers controlled heat to a consumer product selected from the group consisting of a baby carriage, a baby bottle, a blanket, a sleeping bag, pet related products, beauty care related products, a beverage carrier, and a pool covering.

19. The controllable thermal warming device of claim 1, wherein the device delivers controlled heat to a vehicle portion wherein the vehicle portion is selected from the group consisting of a battery, a window, a seat, and an oil system.

20. The controllable thermal warming device of claim 1, having a specific size, design and configuration to satisfy the many stringent requirements of the medical, hospital and personal care industries.

21. The controllable thermal warming device of claim 1 having a disposable covering allowing for the re-use of the controllable thermal warming device.

22. The disposable coverings of claim 21 having specific measurements, configurations to cover and protect said controllable thermal warming devices.

23. The disposable coverings of claim 21 may further comprise securing measures so as to maintain the desired position of said controllable thermal warming devices during use.

24. The disposable coverings of claim 21, wherein the coverings meet the flammability requirements of the National Fire Prevention Standard NFPA 702-1980.

25. The disposable coverings of claim 21, wherein the coverings have liquid repellant characteristics.

26. The disposable coverings of claim 21, wherein the coverings may contain a heat reflective material located so as to direct the heat generated by said controllable thermal warming device in a desired direction.

27. The controllable thermal warming device of claim 1, wherein the device delivers controlled heat to food and food warming related products.

28. The controllable thermal warming device of claim 1, where the device delivers controlled heat to veterinarian related products.

29. The controllable thermal warming device of claim 1, wherein the device delivers controlled heat to wearing apparel wherein the wearing apparel is selected from the group consisting of outdoor, sports, sports related, military and construction.

30. The controllable thermal warming device of claim 1, wherein the power source is AC, DC, Light powered or Solar powered.

* * * * *